(12) United States Patent
Bhatt et al.

(10) Patent No.: US 10,398,461 B2
(45) Date of Patent: Sep. 3, 2019

(54) EXCISING ENDOCAP

(71) Applicant: THE CLEVELAND CLINIC FOUNDATION, Cleveland, OH (US)

(72) Inventors: Amit Bhatt, Cleveland, OH (US); Yutaka Saito, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 849 days.

(21) Appl. No.: 14/535,403

(22) Filed: Nov. 7, 2014

(65) Prior Publication Data

US 2015/0133926 A1 May 14, 2015

Related U.S. Application Data

(60) Provisional application No. 61/901,544, filed on Nov. 8, 2013.

(51) Int. Cl.
*A61B 18/14* (2006.01)
*A61B 17/32* (2006.01)
(Continued)

(52) U.S. Cl.
CPC .. *A61B 17/320016* (2013.01); *A61B 1/00087* (2013.01); *A61B 1/00089* (2013.01);
(Continued)

(58) Field of Classification Search
CPC ...... A61B 2018/00601; A61B 1/00089; A61B 1/0008; A61B 1/00137; A61B 1/00091
See application file for complete search history.

(56) References Cited

U.S. PATENT DOCUMENTS

| 5,573,008 A | * | 11/1996 | Robinson | A61B 10/0266 |
| | | | | 600/567 |
| 6,015,406 A | * | 1/2000 | Goble | A61B 18/1485 |
| | | | | 606/41 |

(Continued)

FOREIGN PATENT DOCUMENTS

| EP | 2417896 A1 | 2/2007 |
| EP | 1834599 A1 | 9/2007 |
| JP | 2005066139 A | 3/2005 |

OTHER PUBLICATIONS

International Search Report and Written Opinion for PCT/US2014/064479, dated Jan. 21, 2015, pp. 1-12.

*Primary Examiner* — Daniel W Fowler
(74) *Attorney, Agent, or Firm* — Tarolli, Sundheim, Covell & Tummino LLP

(57) ABSTRACT

An endoscopic endocap for excising a target portion of a native tissue from a remaining portion of the native tissue during a surgical procedure includes an annular main body. The main body has a proximal end and an oppositely disposed distal end. The distal end includes an extension that protrudes longitudinally beyond a remaining portion of the distal end. An outer surface of the distal end, and an inner surface of the main body, extend longitudinally between the proximal and distal ends. The inner surface defines at least one lumen with an opening terminating at the terminal portion of the distal end. At least one excisor is disposed on the extension with the excisor laterally spaced from the outer surface of the annular main body. The excisor remains stationary with respect to the lumen during use of the excisor to excize the target portion of the native tissue.

20 Claims, 3 Drawing Sheets

(51) Int. Cl.
*A61B 17/00* (2006.01)
*A61B 17/3205* (2006.01)
*A61B 1/00* (2006.01)
*A61B 18/00* (2006.01)

(52) U.S. Cl.
CPC .... *A61B 1/00101* (2013.01); *A61B 17/00234* (2013.01); *A61B 17/3205* (2013.01); *A61B 18/1482* (2013.01); *A61B 18/1492* (2013.01); *A61B 2017/003* (2013.01); *A61B 2017/00269* (2013.01); *A61B 2017/00296* (2013.01); *A61B 2017/00818* (2013.01); *A61B 2017/320056* (2013.01); *A61B 2018/00488* (2013.01); *A61B 2018/00494* (2013.01); *A61B 2018/00595* (2013.01); *A61B 2018/00607* (2013.01)

(56) References Cited

U.S. PATENT DOCUMENTS

| | | | |
|---|---|---|---|
| 7,303,561 B2 | 12/2007 | Ouchi | |
| 7,497,826 B2 | 3/2009 | Ouchi | |
| 9,204,782 B2* | 12/2015 | Nguyen | A61B 17/32056 |
| 9,216,057 B2* | 12/2015 | Goshayeshgar | A61B 18/1492 |
| 9,526,570 B2* | 12/2016 | McLawhorn | A61B 18/1485 |
| 2005/0049454 A1* | 3/2005 | Ouchi | A61B 18/1492 600/105 |
| 2005/0080412 A1* | 4/2005 | Ouchi | A61B 1/00089 606/45 |
| 2007/0203395 A1* | 8/2007 | Mikkaichi | A61B 1/00087 600/127 |
| 2008/0058586 A1* | 3/2008 | Karpiel | A61B 1/00089 600/104 |
| 2008/0132759 A1* | 6/2008 | Miyamoto | A61B 1/00087 600/104 |
| 2009/0247823 A1* | 10/2009 | Yamamoto | A61B 18/1492 600/108 |
| 2010/0174283 A1* | 7/2010 | McNall, III | A61B 18/1485 606/45 |
| 2012/0088965 A1 | 4/2012 | Stokes et al. | |
| 2013/0046138 A1* | 2/2013 | McLawhorn | A61B 1/00087 600/104 |
| 2013/0046300 A1* | 2/2013 | Binmoeller | A61B 18/1492 606/41 |
| 2014/0100570 A1* | 4/2014 | McLawhorn | A61B 18/1485 606/47 |
| 2016/0106497 A1* | 4/2016 | Germain | A61B 17/320016 606/39 |

* cited by examiner

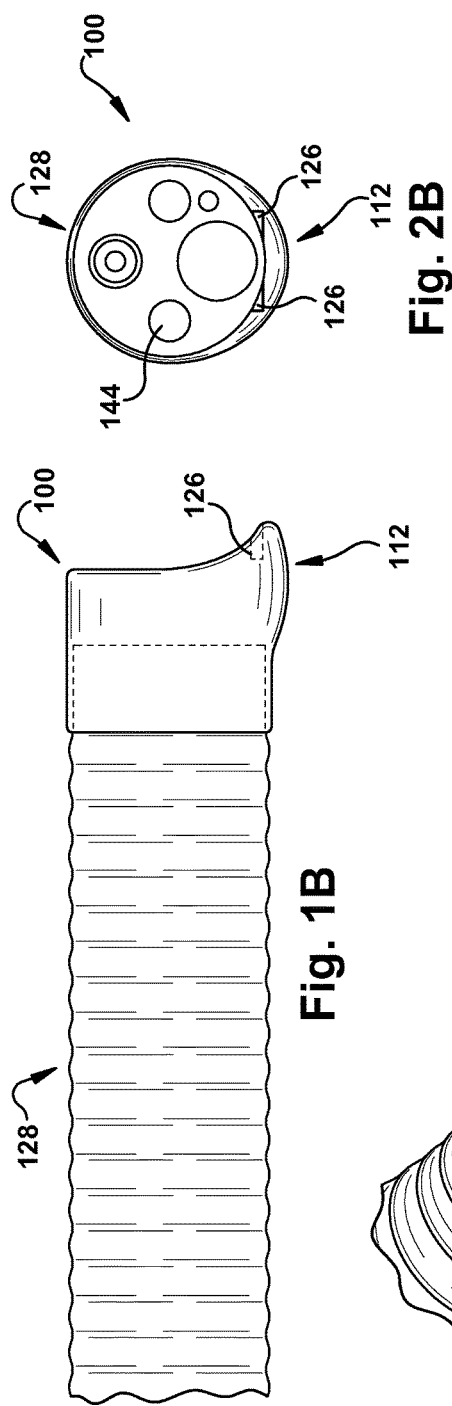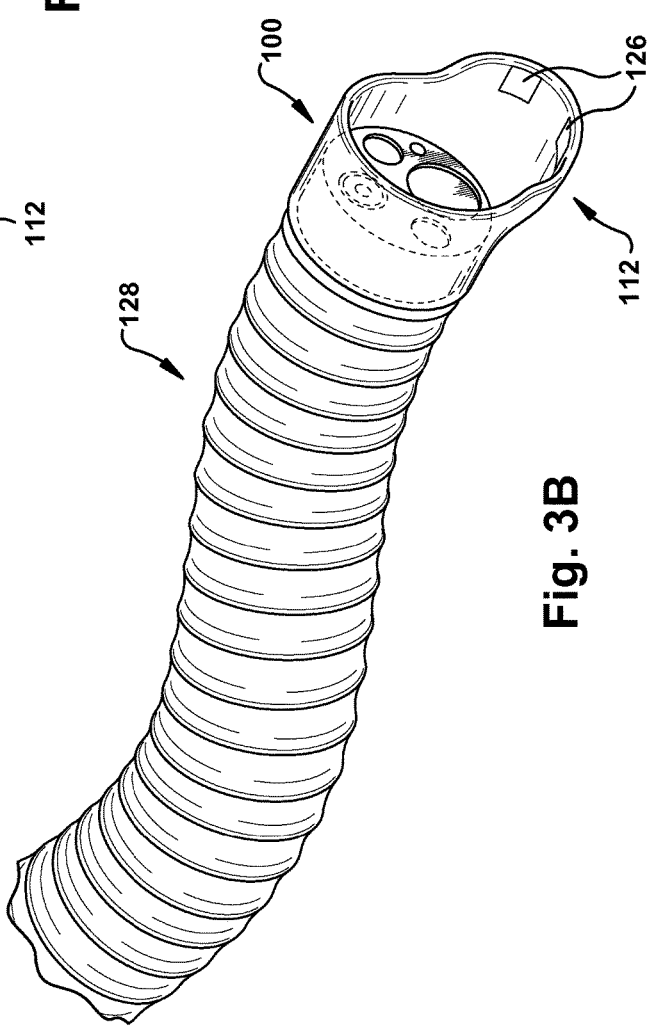

EXCISING ENDOCAP

RELATED APPLICATION

This application claims priority from U.S. Provisional Application No. 61/901,544, filed 8 Nov. 2013, the subject matter of which is incorporated herein by reference in its entirety.

TECHNICAL FIELD

This disclosure relates to an apparatus and method for use of an endoscope and, more particularly, to an excising endocap.

BACKGROUND

During endoscopic surgical procedures such as a peroral endoscopic myotomy or a submucosal tunneling endoscopic resection, a submucosal tunnel may be formed in a portion of the gastrointestinal wall (e.g., the esophagus, the stomach, etc.) using an endoscope. The tunnel is normally formed by dissecting the submucosal layer (between the mucosa layer and the muscle layer) of the gastrointestinal wall using an electrosurgical knife that extends through a channel within the endoscope. Manipulating the knife to a proper position within the channel of the endoscope can be challenging. In addition, it may be desirable in many different surgical procedures to sever or dissect a target portion of a native tissue from a remaining portion.

SUMMARY

In an aspect, an endoscopic endocap for excising a target portion of a native tissue from a remaining portion of the native tissue during a surgical procedure is provided. The endocap includes a longitudinal central axis. An annular main body extends concentrically about the longitudinal central axis. The annular main body has a proximal end and an oppositely disposed distal end longitudinally spaced from the proximal end. The distal end includes an extension that protrudes longitudinally beyond a remaining portion of a front face of a base portion of the distal end. An outer surface of the distal end extends longitudinally between the proximal and distal ends. An inner surface of the main body extends longitudinally between the proximal and distal ends. The inner surface defines at least one lumen. An opening of the at least one lumen terminates at the terminal portion of the distal end. At least one excisor is disposed on the extension such that the at least one excisor is laterally spaced from the outer surface of the annular main body. The at least one excisor is fixedly engaged with the annular main body. The at least one excisor is configured to remain stationary with respect to the lumen during use of the at least one excisor to excise the target portion of the native tissue.

In an aspect, a method of excising a target portion of a native tissue from a remaining portion of the native tissue during a surgical procedure is provided. An endocap is provided. The endocap has a longitudinal central axis and an annular main body extending concentrically about the longitudinal central axis. The annular main body has a proximal end and an oppositely disposed distal end longitudinally spaced from the proximal end. The distal end includes an extension that protrudes longitudinally beyond a portion of a front face of a base portion of the distal end. An outer surface of the main body extends longitudinally between the proximal and distal ends. An inner surface of the main body extends longitudinally between the proximal and distal ends. The inner surface defines at least one lumen. An opening of the lumen terminates at the terminal portion of the distal end. At least one excisor is disposed on the extension such that the at least one excisor is laterally spaced from the outer surface of the annular main body. The at least one excisor is fixedly engaged with the annular main body. The at least one excisor is configured to remain stationary within the lumen during use of the at least one excisor to excise the target portion of the native tissue. The endocap is placed into contact with a surface of the native tissue. The target portion of the native tissue is contacted with the extension. A force is applied to the endocap such that the extension pushes against the native tissue. The at least one excisor is used to excise the target portion of the native tissue upon actuating contact therewith.

BRIEF DESCRIPTION OF THE DRAWINGS

For a better understanding, reference may be made to the accompanying drawings, in which:

FIGS. 1A-1B are schematic side views showing an embodiment of the present invention;

FIGS. 2A-2B are front views showing the embodiment of FIGS. 1A-1B;

FIGS. 3A-3B are plan views showing the embodiment of FIGS. 1A-1B; and

DESCRIPTION OF ASPECTS OF THE DISCLOSURE

Figure 1A:
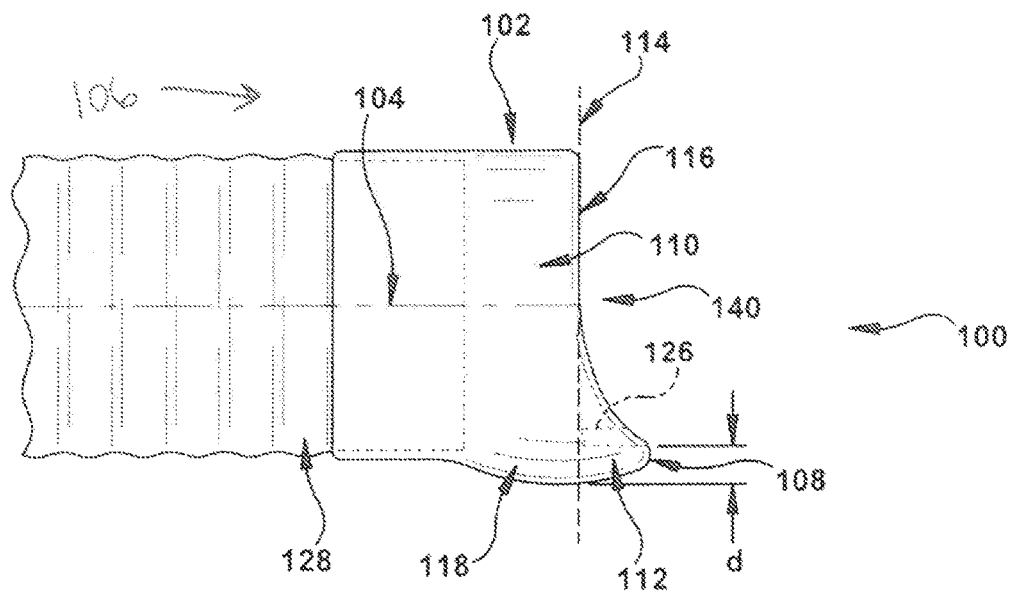
Figure 2A:
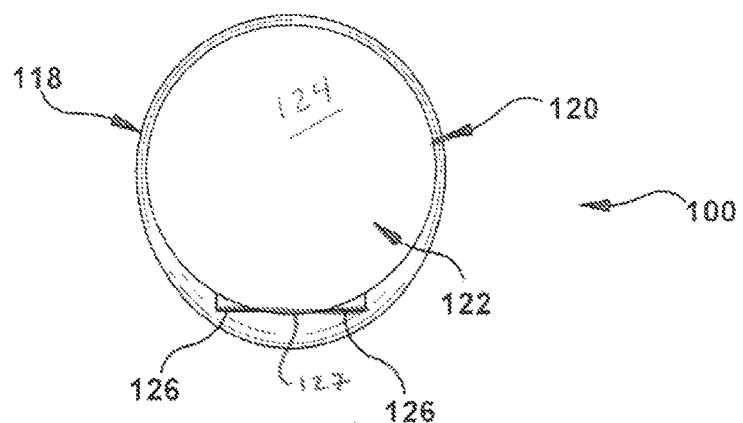
Figure 3A:
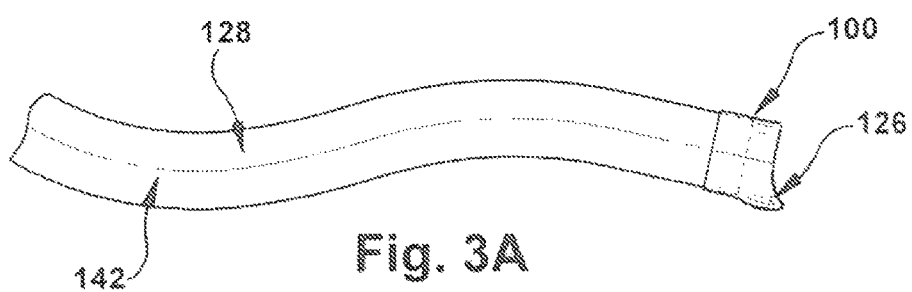

The invention comprises, consists of, or consists essentially of the following features, in any combination.

FIGS. 1A-3B show an endocap 100 configured for excising a desired target portion of a native tissue of a patient from a remaining portion of the native tissue during a surgical procedure. As used herein, the term "excise" refers to removal or separation of at least a portion of the target portion of the native tissue from the remaining portion of the native tissue.

In some instances, the endocap 100 can be used to excise the desired target portion of the native tissue from a top surface of the remaining portion. In other instances, the endocap 100 can be used to excise connecting tissue between the mucosa and muscle layers to facilitate formation of a tunnel in the native tissue.

As shown in FIGS. 1A-3B, the endocap 100 includes an annular main body 102. The main body 102 extends concentrically about a longitudinal central axis 104. The main body 102 has a proximal end 106 that can be mated to an endoscope 128. The main body 102 also has a distal end 108 spaced from the proximal end 106 along the longitudinal axis. The main body 102 includes a base portion 110 and an extension 112 located at the distal end 108. The boundary between the base portion 110 and the extension 112 is defined by a reference plane 114. The base portion 110 includes a terminal portion 116 that is co-planar with at least a portion of the reference plane 114.

The extension 112 protrudes longitudinally beyond (i.e., "extends distally past") a remaining portion of a front face 140 of the base portion 110. That is, the distalmost surface of the extension 112 is located distally further away from the distal end 108 than is the front face 140 of the base portion 110, as shown in especially FIG. 1A. The extension 112 is configured to contact the native tissue to bulge the desired target portion away from the rest of the native tissue. In other words, the extension 112 is configured such that force exerted on the endocap 100 by the endoscope 128 causes the extension 112 to move at least a portion of the native tissue 138 to bring the target portion 134 into sufficient proximity with the excisor 126 to facilitate excision of the target portion 134.

The main body 102 further includes an outer surface 118 and an inner surface 120 that each extend longitudinally between the proximal and distal ends 106 and 108. The inner surface 120 defines a lumen 122 located within the main body 102. An opening 124 of the lumen 122 terminates at the terminal portion 116 of the main body 102.

One or more excisors 126 are disposed on the extension 112. The excisors 126 may be spaced, such as inward by distance "d", from the outer surface 118 of the main body 102, when desired to protect the underlying remaining portion of the native tissue. The excisors 126 are fixedly engaged with a portion of the extension 112. A portion of each excisor 126 is exposed within the lumen 122.

In one example, the excisors 126 can be an electrocautery device (e.g., a Bovie knife) connected to a power supply with a power supply line. In this electrocautery example, the endocap 100 can also or instead be used for hemostasis, or selective electrically-affected coagulation of bleeding vessels. In another example (shown schematically at 127 in FIG. 2A), the excisors 126 can be any suitable device to mechanically shave the target portion, such as blades—in such instance, the excisors 126 could protrude outward in any suitable direction, angle, length, or other physical feature from the remaining portions of the endocap 100. Two excisors 126 are shown in several of the Figures, but one of ordinary skill in the art can readily provide any suitable number, shape, location, configuration, or other options for the excisor(s) 126 for a particular use environment.

FIGS. 4A-4D show the endocap 100 of the previous Figures in use during an endoscopic procedure in which the endocap 100 is carried by an endoscope 128 between mucosa and muscle layers 130 and 132, respectively, of the native tissue 138. In the example shown in the Figures, the endocap 100 can be configured to excise a desired target portion 134 of a native tissue from a remaining portion 136 of the native tissue 138.

Figure 4A:
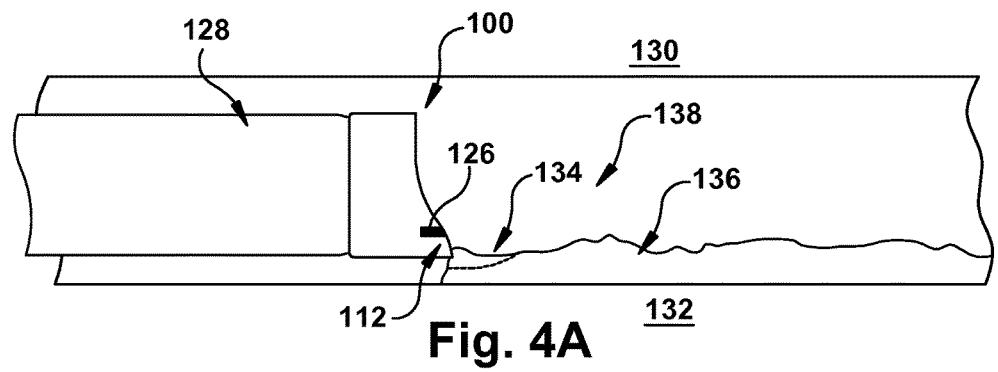
FIGS. 4A-4D show an example sequence of use for the embodiment of FIGS. 1A-1B.

The endocap 100 is mated with the endoscope 128 in any suitable manner and placed into contact with the target portion 134 of the native tissue 138 (FIG. 4A). It is contemplated that a power supply line 142 associated with the endoscope 128 will be operatively attached to at least one excisor 126 for selective operation thereof, in the depicted electrocautery procedure. While FIGS. 4A-4D depict the extension 112, and thus the excision, as occurring at a lowermost position with respect to the endoscope 128, one of ordinary skill in the art will realize that the extension 112 could be located, or turned to, any point along the circumference of the base portion 110. Indeed, it is contemplated that a plurality of radially spaced extensions (not shown) could be used to selectively simultaneously and/or separately perform excisions upon spaced-apart target portions during the course of a single surgical procedure.

Figure 4B:
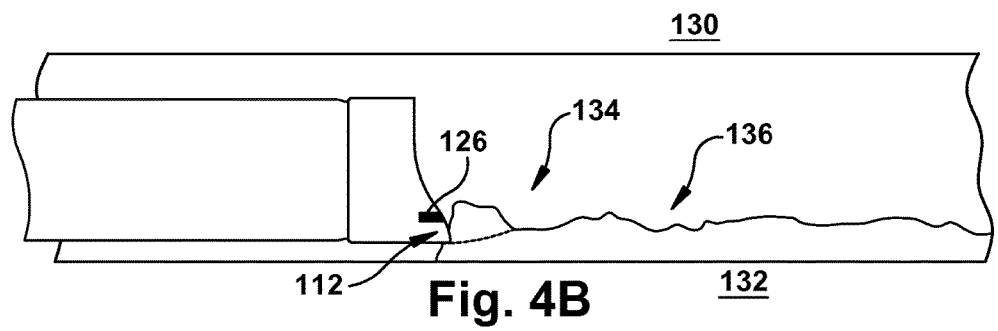
Figure 4C:
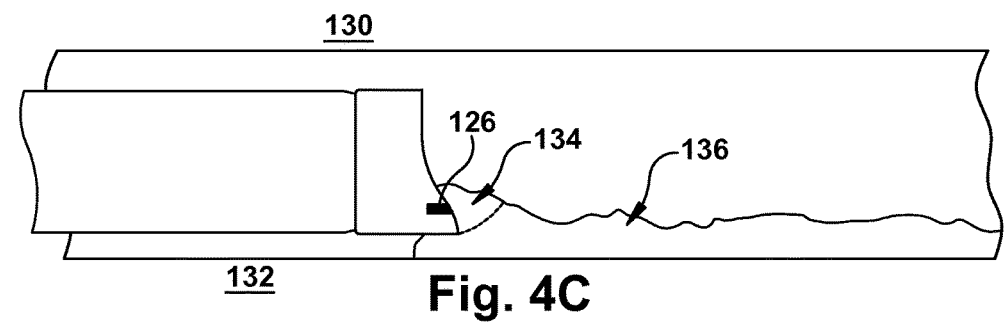
Figure 4D:
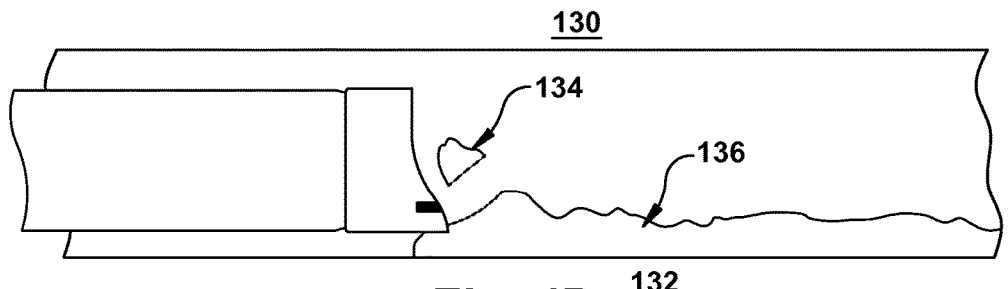

A surgeon then maneuvers the endoscope 128 towards the desired target portion 134 of the native tissue 138 so that the extension 112 pushes against the tissue and bulges the target portion 134 to a position above the excisors 126 (FIG. 4B). The excisors 126 then begin to "shave" the target portion 134 of the native tissue 138 upon actuating contact (FIG. 4C). The term "shave" is used herein to indicate removal of a topmost layer of material from a remaining bulk of the material by passing an excisor 126 under the layer to be removed. An "actuating contact" here denotes a situation where the excisor 126 is in suitable proximity to the target portion 134 that an electrical controller, mechanical touch, or other "actuating" event is controlled by the user and/or automatically occurs to cause the excisors 126 to affect the target portion 134 in the desired manner. An "actuating contact" need not be actual direct contact, but could instead be a desired proximity, for a particular use environment and as determined by one of ordinary skill in the art for a desired performance of the endocap 100.

The target portion 134 can be shaved from the remaining portion 136 of the native tissue 138 (FIG. 4D) using an electrical means (e.g., electrocautery), a mechanical means (e.g., a sharpened blade) and/or any other suitable means for severing or otherwise physically altering the target portion 134 via direct or indirect contact, and/or suitable proximity, with the endocap 100. A suction device (not shown) may extend through the lumen 122 to capture the released target portion 134 after shaving occurs. The endoscope 128 can be used to continuously and/or intermittently shave a plurality of target portions 134 from the remaining portion(s) 136 of tissue, in parallel or in sequence.

In another example (not shown), the endocap 100 can be configured to dissect connecting tissue between layers of the native tissue 138 until a desired structure, such as a tunnel with desired dimensions, has been formed in the native tissue 138 by excision of connecting tissue from the native tissue 138. This example configuration may be helpful, e.g., in crafting a submucosal tunnel (e.g., for peroral endoscopic myotomy or a submucosal tunneling endoscopic resection) without the current need to occupy/use one of the endoscope's 128 accessory channels 144 during formation of the tunnel.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An endoscopic endocap for excising a target portion of a native tissue from a remaining portion of the native tissue during a surgical procedure, the endocap comprising:
   a longitudinal central axis;
   an annular main body extending concentrically about the longitudinal central axis, the annular main body having a proximal end,
   an oppositely disposed distal end longitudinally spaced from the proximal end, the distal end including an extension that protrudes longitudinally beyond a remaining portion of a front face of a base portion of the distal end,
   an outer surface extending longitudinally between the proximal and distal ends, and
   an inner surface extending longitudinally between the proximal and distal ends, the inner surface defining at least one lumen, an opening of the at least one lumen terminating at a terminal portion of the distal end;
   at least one excisor disposed on the extension such that the at least one excisor is laterally spaced from the outer surface of the annular main body, the at least one excisor being fixedly engaged with the annular main body, the at least one excisor being configured to remain stationary with respect to the lumen during use of the at least one excisor to excise the target portion of the native tissue, the at least one excisor including a mechanical blade.

2. The endoscopic endocap of claim 1, wherein at least one excisor is an electrocautery device.

3. The endoscopic endocap of claim 2, wherein a power supply line, associated with an endoscope for carrying the endocap, is operatively attached to the at least one excisor for selective operation thereof.

4. The endoscopic endocap of claim 1, wherein an entirety of the at least one excisor is in direct contact with the extension.

5. The endoscopic endocap of claim 1, wherein a substantially laterally oriented reference plane defines a boundary between the base portion and the extension, and the extension includes a substantially laterally extending distal extension face bounded laterally by the outer and inner surfaces of the endocap.

6. The endoscopic endocap of claim 5, wherein the distal extension face is longitudinally convex with respect to the reference plane.

7. The endoscopic endocap of claim 5, wherein at least a portion of the distal extension face is for contacting the remaining portion of the patient tissue concurrently with contact of the target portion of the native tissue with the at least one excisor.

8. The endoscopic endocap of claim 5, wherein at least a portion of the distal extension face is for contacting the remaining portion of the patient tissue before contact of the target portion of the native tissue with the at least one excisor occurs.

9. The endoscopic endocap of claim 5, wherein the at least one excisor is substantially longitudinally proximal from the distal extension face.

10. A method of excising a target portion of a native tissue from a remaining portion of the native tissue during a surgical procedure, comprising the steps of:
    providing an endocap having:
      a longitudinal central axis,
      an annular main body extending concentrically about the longitudinal central axis, the annular main body having a proximal end,
      an oppositely disposed distal end longitudinally spaced from the proximal end, the distal end including an extension that protrudes longitudinally beyond a portion of a front face of a base portion of the distal end,
      an outer surface extending longitudinally between the proximal and distal ends, and
      an inner surface extending longitudinally between the proximal and distal ends, the inner surface defining at least one lumen, an opening of the lumen terminating at a terminal portion of the distal end;
    at least one excisor disposed on the extension such that the at least one excisor is laterally spaced from the outer surface of the annular main body, the at least one excisor being fixedly engaged with the annular main body, the at least one excisor being configured to remain stationary within the lumen during use of the at least one excisor to excise the target portion of the native tissue;
    placing the endocap into contact with a surface of the native tissue;
    contacting the target portion of the native tissue with the extension;
    applying a force to the endocap such that the extension pushes against the native tissue; and
    using the at least one excisor to excise the target portion of the native tissue upon actuating contact therewith, including mechanically excising the target portion of the native tissue.

11. The method of claim 10, wherein using the at least one excisor includes applying electrocauterizing energy to the target portion of the native tissue.

12. The method of claim 11, including coagulating blood via hemostasis during the application of electrocauterizing energy to the target portion of the native tissue.

13. The method of claim 10, wherein applying a force to the endocap includes causing the extension to move at least a portion of the native tissue to bring the target portion into sufficient proximity with the at least one excisor to facilitate excision of the target portion.

14. The method of claim 10, wherein providing an endocap includes operatively attaching a power supply line, associated with an endoscope for carrying the endocap, to at least one excisor for selective operation thereof.

15. The method of claim 10, wherein providing an endocap includes providing an endocap having an entirety of the at least one excisor in direct contact with the extension.

16. The method of claim 10, wherein providing an endocap includes defining a boundary between the base portion and the extension with a substantially laterally oriented reference plane, and wherein the extension includes a substantially laterally extending distal extension face bounded laterally by the outer and inner surfaces of the endocap.

17. The method of claim 16, wherein the distal extension face is longitudinally convex with respect to the reference plane.

18. The method of claim 16, wherein placing the endocap into contact with a surface of the native tissue includes contacting the remaining portion of the patient tissue with at least a portion of the distal extension face concurrently with contact of the target portion of the native tissue with the excisor.

19. The method of claim 16, wherein placing the endocap into contact with a surface of the native tissue includes contacting the remaining portion of the patient tissue with at least a portion of the distal extension face before contact of the target portion of the native tissue with the excisor occurs.

20. The method of claim 16, wherein providing an endocap includes placing the at least one excisor substantially longitudinally proximal from the distal extension face.

\* \* \* \* \*